United States Patent

Bang et al.

Patent Number: 5,605,895
Date of Patent: Feb. 25, 1997

[54] CEPHALOSPORIN ANTIBIOTICS AND PROCESSES FOR PREPARATION THEREOF

[75] Inventors: Chan S. Bang; Yong Z. Kim; Jae H. Yeo; Jong C. Lim; Young M. Woo; Hun S. Oh; Duk H. Yang; Sam S. Kim, all of Daejeon; Se H. Kim; Jae H. Jeon, both of Seoul; Tae H. Lee, Daejeon; Sung I. Kim, Inchun; Mi K. Seo; Jae W. Lee, both of Seoul, all of Rep. of Korea

[73] Assignee: Lucky, Ltd., Seoul, Rep. of Korea

[21] Appl. No.: 277,629

[22] Filed: Jul. 20, 1994

[30] Foreign Application Priority Data

Jul. 23, 1993 [KR] Rep. of Korea ............... 93-14063

[51] Int. Cl.$^6$ .................... A61K 31/545; C07D 501/36
[52] U.S. Cl. ......................... 514/206; 540/227
[58] Field of Search ............................ 540/227; 514/206

[56] References Cited

U.S. PATENT DOCUMENTS 5,234,920   8/1993   Okita et al. ................. 514/202
5,292,733   3/1994   Kim et al. .................. 514/206

*Primary Examiner*—Yogendra N. Gupta
*Attorney, Agent, or Firm*—Birch, Stewart, Kolasch & Birch, LLP

[57] ABSTRACT

The present invention relates to a cephalosporin compound represented by the following general formula (I), its pharmaceutically acceptable non-toxic salt, physiologically hydrolyzable ester, hydrate or solvate, or isomers thereof, which is useful as an antibiotic agent:

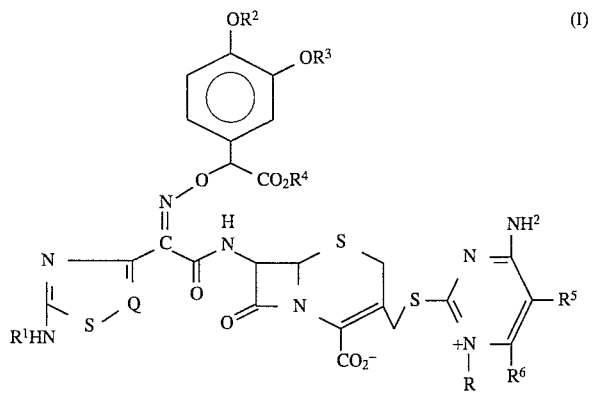

in which $R^1$ represents hydrogen or an amino-protecting group, $R^2$ and $R^3$ can be identical or different and each represent hydrogen or a hydroxy-protecting group, or $R^2$ and $R^3$ together can form a diol-protecting cyclic group, $R^4$ represents hydrogen or a carboxyl-protecting group, $R^5$ represents hydrogen, $C_{1-4}$ alkyl, alkoxycarbonyl, carboxyl or sulfomethyl, $R^6$ represents hydrogen, amino or substituted amino, and $R^7$ represents $C_{1-4}$ alkyl, amino or substituted amino, or $R^5$ and $R^6$ together with the carbon atoms to which they are attached can form a 3 to 7-membered cyclic group, or $R^6$ and $R^7$ together with the carbon and nitrogen atoms to which they are attached can form a 3 to 7-membered heterocyclic ring which may optionally contain additional heteroatoms such as nitrogen and/or oxygen and which may be substituted with the substituents selected from $C_{1-4}$ alkyl, amino and substituted amino, and Q represents CH or N.

3 Claims, No Drawings

CEPHALOSPORIN ANTIBIOTICS AND PROCESSES FOR PREPARATION THEREOF

BACKGROUND OF THE INVENTION

1. Field of the Invention

The present invention relates to a novel cephalosporin compound represented by the following general formula (I):

$$\text{(I)}$$

, its pharmaceutically acceptable non-toxic salt, physiologically hydrolyzable ester, hydrate and solvate, and isomer thereof, in which $R^1$ represents hydrogen or an amino-protecting group, $R^2$ and $R^3$ can be identical or different and each represent hydrogen or a hydroxy-protecting group, or $R^2$ and $R^3$ together can form a diol-protecting cyclic group, $R^4$ represents hydrogen or a carboxyl-protecting group, $R^5$ represents hydrogen, $C_{1-4}$ alkyl, alkoxycarbonyl, carboxyl or sulfomethyl, $R^6$ represents hydrogen, amino or substituted amino, and $R^7$ represents $C_{1-4}$ alkyl, amino or substituted amino, or $R^5$ and $R^6$ together with the carbon atoms to which they are attached may form a 3 to 7-membered cyclic group, or $R^6$ and $R^7$ together with the carbon and nitrogen atoms to which they are attached can form a 3 to 7-membered heterocyclic ring which may optionally contain additional heteroatoms such as nitrogen and/or oxygen and which may be substituted with the substituent selected from $C_{1-4}$ alkyl, amino and substituted amino, and Q represents CH or N.

The present invention also relates to a process for preparation of the compound of formula (I), as defined above, and to a pharmaceutical composition containing the compound of formula (I) as an active ingredient.

2. Background Art

Cephalosporin antibiotics have been widely used for treating diseases caused by pathogenic bacteria in human and animals and are particularly useful for treating diseases caused by bacteria which are resistant to other antibiotics such as penicillin compounds and for treating penicillin-hypersensitive patients. In most cases, it is preferable to use antibiotics which are active against both of gram-positive and gram-negative microorganisms. However, it has been well known that an antimicrobial activity of such cephalosporin antibiotics is greatly influenced by the substituent on 3- or 7-position of the cephem nucleus. Accordingly, it has been attempted to develop an antibiotic compound which shows a high antibacterial activity against a broad range of gram-positive and gram-negative strains and is very stable to β-lactamse produced by various gram-negative strains and is also very stable in the living tissues. As a result thereof, heretofore, numerous cephalosporin antibiotics wherein various substituents are introduced into the 7-β acylamino moiety and the 3-position of cephem nucleus have been developed.

For example, Japanese Laid-open Patent Publication No. (sho) 54-9296 very broadly discloses a cephalosporin derivative represented by the following general formula (A) having a substituent A on the 3-position of cephem nucleus:

$$\text{(A)}$$

In the specification of said Japanese Laid-open Patent Publication, it is generally disclosed that the substituent A on the 3-position is hydrogen, alkyloxy or alkenyloxy group which can be optionally substituted, halogen, or a $-CH_2Y$ group wherein Y represents hydrogen, halogen or a residue derived from nucleophilic compounds such as $-SR$, and particularly, when Y is $-SR$, R is a 5 to 8-membered heterocyclic group which can be substituted. In this patent specification, as the specific example of the 5- to 8-membered heterocyclic group pyridyl or pyrimidinyl group which can be substituted is mentioned but there is no mention of 3-substituted 4-aminopyrimidinium group in a quaternary form as present in the compound of the present invention.

Meanwhile, European Patent Application No. 87304896.1 of Mitzyoshi et. al., discloses a cephalosporin compound represented by the following general formula (B):

$$\text{(B)}$$

in which $R_4$ is amino which may be protected, $R_5$ represents a group having the following general formula (B-1) or (B-2), $$\text{(B-1)} \quad \text{(B-2)}$$

$R_6$ represents lower alkenyl, a N-containing 5- or 6-membered heterocyclic group which may be substituted, acylamino, or lower alkyl which may be substituted, $R_7$ and $R_8$ can be identical or different and each represent hydrogen, lower alkyl, amino, acylamino, carboxyl, carbamoyl, thiocarbamoyl or lower alkoxycarbonyl, $R_9$ and $R_{10}$ independently of each other represent lower alkyl, and V' and W' can be identical or different and represent a group —CH= or —N=.

In the specification of said Japanese Laid-open Patent Application, as the substituent on 3-position various heterocyclic groups including the groups of formulae (B-1) and (B-2), which may be substituted with hydrogen, lower alkyl, amino, etc., are described. In this specification, however, only alkyl-substituted pyrimidiniumthiomethyl group is specifically mentioned, which is completely distinguished from 3-substituted pyrimidiniumthiomethyl group having an amino group on 4-position.

Thus, the present inventors have extensively studied to develop cephalosporin antibiotics having a potent antimicrobial activity and a broad antibacterial spectrum. As a result, we have succeeded in developing cephalosporin compounds represented by the following general formula (C) having various 4,6-diaminopyrimidinium moiety on C-3 position (see, Korean Patent Nos. 47728, 47754, 47755 and 47756):

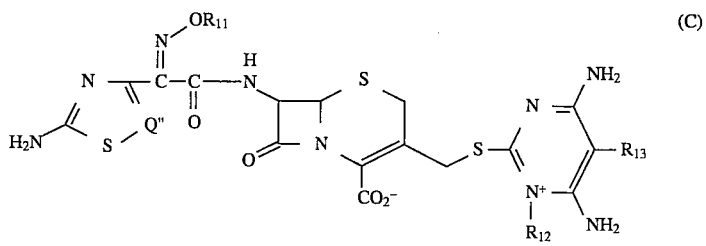

(C)

in which $R_{11}$ represents $C_{1-4}$ alkyl, $C_{3-4}$ alkenyl, $C_{3-C4}$ alkynyl or a group $C(R^A)(R^B COOH)$, $R_{12}$ represents $C_{1-4}$ alkyl, $C_{3-4}$ alkenyl, $C_{3-4}$ cycloalkyl, substituted or unsubstituted amino, or substituted or unsubstituted phenyl, $R_{13}$ represents hydrogen or $C_{1-4}$ alkyl, and Q" represents CH or N.

However, in the specifications of the above prior patents by the present inventors the compounds having a substituted aminopy-rimidiniumthiomethyl group in quaternary form are described, but there is no mention and suggestion on the compounds which can contain (Z)-2-(2-aminothiazol-4-yl)-2-(α-carboxy substituted phenylmethoxyimino)acetamido group on 7-position as described in the present invention.

Meanwhile, PCT/JP86/00140 discloses the cephem compound represented by the following general formula (D):

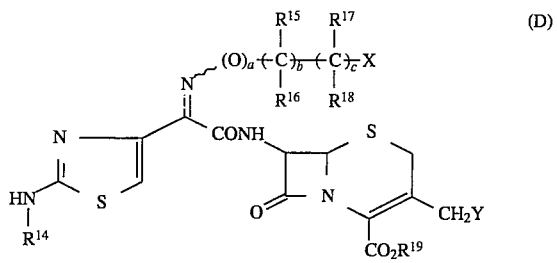

(D)

in which $R^{14}$ represents hydrogen or an amino-protecting group, $R^{15}$ and $R^{16}$ represent hydrogen, methyl, carboxyl, protected carboxyl or oxygen atom, $R^{17}$ and $R^{18}$ represent hydrogen or oxygen atom, $R^{19}$ represents hydrogen or a carboxyl-protecting group, a, b and c are an integer of 0 or 1, and X represents hydrogen, hydroxyl or a group of formula

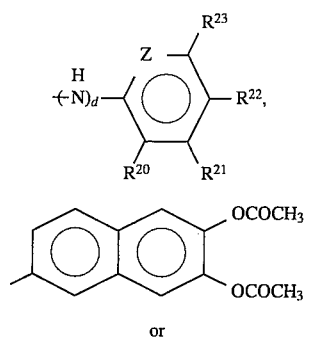

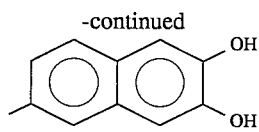

-continued

The specification of the above PCT application broadly describes the compounds having the substituent (Z)-2-(2-amino-thiazol-4-yl)-2-(α-carboxy substituted phenylmethoxyimino)acetamido group on 7β-position as described in the present invention and also having a heterocyclothiomethyl group, particularly triazolopyrimidylthiomethyl, thiazolopyrimidylthiomethyl, and the like group, on C-3 position. However, such groups are completely different from 4-amino-3-substituted pyrimidiniumthiomethyl group in quaternary form as in the present invention. In addition, there is no mention or suggestion on such quaternary group.

In addition, European Patent Application No. 87308525.2 describes the cephem compound represented by the following general formula (E):

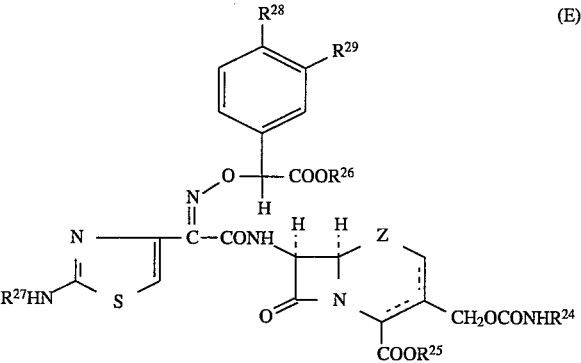

(E)

in which $R^{24}$ represents hydrogen, or $C_{1-4}$ alkyl substituted with 1 to 3 halogen atom(s), $R^{25}$ and $R^{26}$ represent hydrogen or a carboxyl-protecting group, $R^{27}$ represents hydrogen or an amino-protecting group, $R^{28}$ and $R^{29}$ represent hydroxy or substituted hydroxy, or $R^{28}$ and $R^{29}$ together form a protected cyclic diol group, Z represents >S or >S→O, and a dotted line denotes 2-cephem or 3-cephem compound.

However, in the above European patent the substituent introduced into $C_3$-position is different from the C-3 substituent of the present invention.

Thus, the present inventors have attempted to develop a compound having more potential antibacterial activity on the basis of the fact that the compounds disclosed in the previously described Korean Patent Nos. 47728, 47754, 47755 and 47756, i.e., cephalosporin compounds containing an optionally substituted pyrimidiniumthiomethyl group having a positive-charged structure on C-3 position have high antibacterial activity.

As one of such attempts we have tried to introduce a new substituent into C-7 position without any change in the C-3 substituent. As a result, we have identified that cephalosporin compounds having (Z)-2-(2-aminothiazol-4-yl)-2-(α-carboxy substituted phenylmethoxyimino)acetamido group on 7-β position and, at the same time, 3-substituted 4-aminopy-rimidiniumthiomethyl on C-3 position exhibit a potent antibacterial activity against various pathogenic organisms including β-lactamse producing gram-negative strains and further have a more improved pharmacokinetic property. Thus, now we have completed the present invention.

Therefore, it is an object of the present invention to provide a novel cephalosporin compound having the general formula (I), as defined above, which has a potent antimicrobial activity, broad antibacterial spectrum and improved pharmacokinetic properties.

It is a further object of the present invention to provide a process for preparing the novel cephalosporin compound of formula (I).

Further, it is another object of the present invention to provide a pharmaceutical composition containing the novel cephalosporin compound of formula (I) as an active ingredient.

The foregoing has outlined some of the more pertinent objects of the present invention. These objects should be construed to be merely illustrative of some of the more pertinent features and applications of the invention. Other many beneficial results can be obtained by applying the disclosed invention in a different manner of modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

In one aspect, the present invention relates to a cephalosporin antibiotic compound represented by the following general formula (I), having (Z)-2-(2-aminothiazol-4-yl)-2-(α-carboxy substituted phenylmethoxyimino)acetamido group on 7-β position and, at the same time, (3-substituted 4-aminopyrimidinium)thiomethyl group on C-3 position:

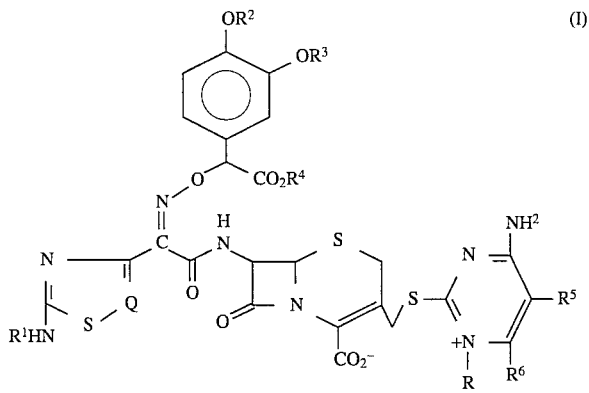

, its pharmaceutically acceptable non-toxic salt, physiologically hydrolyzable ester, hydrate and solvate, and isomer thereof, in which $R^1$ represents hydrogen or an amino-protecting group, $R^2$ and $R^3$ can be identical or different and each represent hydrogen or a hydroxy-protecting group, or $R^2$ and $R^3$ together can form a diol-protecting cyclic group, $R^4$ represents hydrogen or a carboxyl-protecting group, $R^5$ represents hydrogen, $C_{1-4}$ alkyl, alkoxycarbonyl, carboxyl or sulfomethyl, $R^6$ represents hydrogen, amino or substituted amino, and $R^7$ represents $C_{1-4}$ alkyl, amino or substituted amino, or $R^5$ and $R^6$ together with the carbon atoms to which they are attached can form a 3 to 7-membered cyclic group, or $R^6$ and $R^7$ together with the carbon and nitrogen atoms to which they are attached can form a 3 to 7-membered heterocyclic ring which may optionally contain additional heteroatoms such as nitrogen and/or oxygen and which may be substituted with the substituent selected from $C_{1-4}$ alyl, amino and substituted amino, and Q represents CH or N.

In the definitions of the substituents for the compound of formula (I) above, $R^1$ and $R^4$ are most preferably hydrogen and $R^2$ and $R^3$ can be identical or different and are preferably hydrogen or acetyl. $R^5$ is preferably hydrogen, methyl, carboxyl or sulfomethyl, $R^6$ is preferably hydrogen or amino, and $R^7$ is preferably methyl or amino group. In addition, the preferred example of the cycle which may be formed by $R^5$ and $R^6$ together with the carbon atoms to which they are attached is cyclopentane or cyclohexane. The preferred example of the heterocyclic ring which can be formed by $R^6$ and $R^7$ together with the carbon and nitrogen atoms to which they are attached is imidazole or triazole. In this case, the preferred example of the possible substituent for the heterocyclic ring is methyl or amino group.

In the formula (I) above, the carbon atom to which a 3,4-substituted phenyl moiety is attached is an asymmetric center. Therefore, the compound of formula (I) can be present as a diastereomeric isomer. Thus, individual diastereomeric isomer and the mixture thereof are included in the scope of the present invention. The compound of formula (I) according to the present invention can be present as geometric isomers including synisomer or a syn- and anti-isomeric mixture containing 90% or more of syn-isomer. In addition, since the aminothiazole group in the compound of formula (I) can be present as a tautomeric isomer with the aminothiazoline group, such tautomer can also be included within the scope of the present invention.

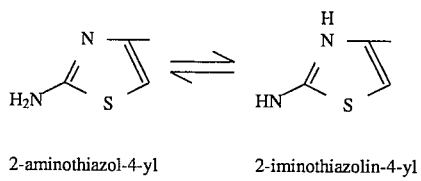

2-aminothiazol-4-yl        2-iminothiazolin-4-yl

The pharmaceutically acceptable non-toxic salt of the compound of formula (I) includes salts with inorganic acids such as hydrochloric acid, hydrobromic acid, phosphoric acid, sulfuric acid, etc., salts with organic carboxylic acids such as acetic acid, trifluoroacetic acid, citric acid, formic acid, maleic acid, oxalic acid, succinic acid, benzoic acid, tartaric acid, fumaric acid, mandelic acid, ascorbic acid, malic acid, etc. or salts with sulfonic acids such as methanesulfonic acid, paratoluenesulfonic acid, etc., and salts with other acids which are conventionally used in penicillin and cephalosporin fields. These acid addition salts are prepared according to a conventional technique. In addition, the compound of formula (I) can also form a non-toxic salt with base. The base which can be used for this purpose includes inorganic bases such as alkali metal hydroxides (for example, sodium hydroxide or potassium hydroxide), alkaline earth metal hydroxides (for example, calcium hydroxide), sodium hydrogen carbonate, potassium hydrogen carbonate, sodium carbonate, potassium carbonate, calcium carbonate, etc., or organic bases such as amino acids.

The physiologically hydrolyzable ester of the compound of formula (I) includes, for example, indanyl, phthalidyl, methoxymethyl, pivaloyloxymethyl, glycyloxymethyl, phenylglycyloxymethyl, 5-methyl-2-oxo-1,3-dioxolan-4-yl methyl ester and other physiologically hydrolyzable esters which are conventionally used in the technical field of penicillins and cephalosporins. Such esters can be prepared according to the known method.

The hydrates and solyates of the compound of formula (I) are also included within the scope of the present invention.

In another aspect, the present invention provides a process for preparing the compound of formula (I). According to the process of the present invention, the compound of formula (I):

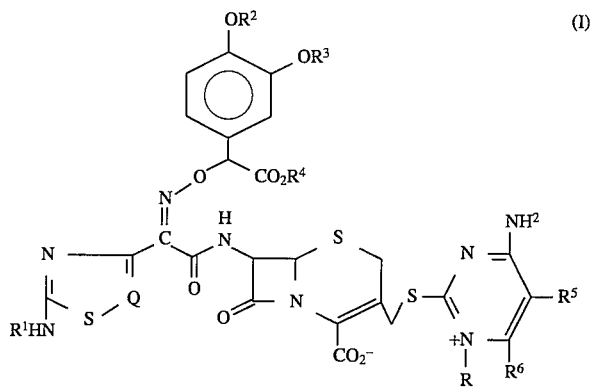

in which $R^1$, $R^2$, $R^3$, $R^4$, $R^5$, $R^6$, $R^7$ and Q are defined as previously described, its pharmaceutically acceptable non-toxic salts, its physiologically hydrolyzable esters, hydrates and solyates can be prepared by a process characterized in that a compound having the following general formula (II):

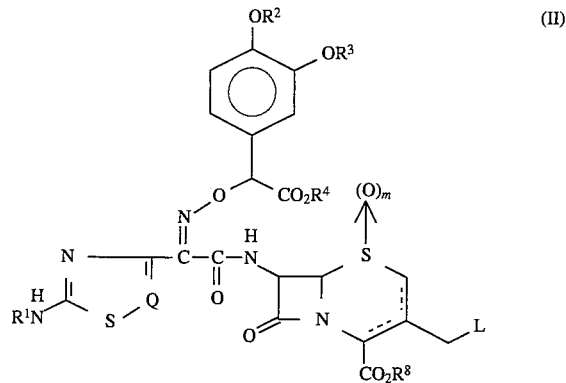

in which $R^1$, $R^2$, $R^3$, $R^4$, and Q are defined as in formula (I) $R^8$ represents hydrogen or a carboxyl-protecting group, L is a leaving group and m is 0 or 1, is reacted with a compound having the following general formula (III):

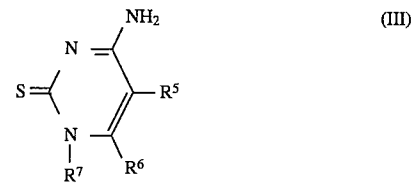

in which $R^5$, $R^6$ and $R^7$ are defined as in formula (I), in the presence of a solvent and, if required, before or after the reaction the amino-protecting group or the carboxyl-protecting group is removed or the S-oxide $(S \rightarrow (O)_m)$ is reduced.

In the above formulae, the amino-protecting group for $R^1$ means a conventional amino-protecting group such as acyl, substituted or unsubstituted ar(lower)alkylo (e.g. benzyl, diphenylmethyl, triphenylmethyl, 4-methoxybenzyl, etc.), halo(lower)alkyl (e.g. trichloromethyl, trichloroethyl, etc.), tetrahydropyranyl, substituted phenylthio, substituted alkylidene, substituted aralkylidene, etc. Suitable acyl group as the amino-protecting group may be aliphatic and aromatic acyl groups or acyl groups having heterocyclic ring. Example of such acyl groups may include $C_{1-6}$ lower alanoyl (e.g. formyl, acetyl, etc.), $C_{2-6}$ alkoxycarbonyl (e.g. methoxycarbonyl, ethoxycarbonyl, etc.), lower alkanesulfonyl (e.g. methanesulfonyl, ethanesulfonyl, etc.), or ar(lower)alkoxycarbonyl (e.g. benzyloxycarbonyl, etc.), and the like. The above-mentioned acyl groups can contain suitable substituents selected from 1 to 3 halogen, hydroxy, cyano, nitro and the like. In addition, the reaction product of amino group with silane, boron or phosphorus compound may also act as the amino-protecting group.

As the carboxyl-protecting group for $R^4$ and $R^8$, any of the conventional groups which can be readily removed under mild condition can be suitable. Specific example thereof includes (lower)alkyl ester (e.g. methyl ester, t-butyl ester, etc.), (lower) alkenyl ester (e.g. vinyl ester, allyl ester, etc.), (lower)alkoxy(lower) alkyl ester (e.g. methoxymethyl ester, etc.), (lower)alkylthio(lower)alkyl ester (e.g. methylthiomethyl ester, etc.), halo(lower)alkyl ester (e.g. 2,2,2-trichloroethyl ester, etc.), substituted or unsubstituted aralkyl ester (e.g. benzyl ester, p-nitrobenzyl ester, p-methoxybenzyl ester, etc.) or silyl ester, and the like.

The hydroxy-protecting group for $R^2$ and $R^3$ may include acyl group [for example, formyl or a —$COR^a$ group wherein $R^a$ is $C_{1-8}$ alkyl (e.g. acetyl)], alkoxycarbonyl group [for example, a —$CO_2R^a$ (wherein $R^a$ is $C_{1-8}$ alkyl)], silyl group [for example, $(C_{1-4}$ alkyl)silyl such as trimethylsilyl or t-butyldimethylsilyl], or a borate [—B $(OR^b)_2$] group (wherein $R^b$ is $C_{1-4}$ alkyl); and the cyclic diol-protecting group which can be formed by $R^5$ and $R^6$ includes $C_{1-20}$ alkylidenedioxy group (for example, methylenedioxy, ethylenedioxy or isopropylidenedioxy), alkylidenedioxy group containing one or more substituent(s) (for example, methoxymethylenedioxy, diphenylmethylenedioxy or carbonyldioxy), cyclic borate group (for example, —OB(OH)O—), cyclic phosphate group (for example, —OP(O)(OH)O— or —OP(O)(OR$^b$)O— wherein $R^b$ is defined as previously described) or di($C_{1-4}$ alkyl)silyldioxy group (for example, dimethylsilyldioxy), and the like.

The above-mentioned amino-protecting group, hydroxy-protecting group, cyclic diol-protecting group and carboxyl-protecting group can be readily removed by hydrolysis, reduction, etc. under mild condition to form free amino, hydroxy or carboxyl group and are appropriately selected depending on the chemical properties of the compound of formula (I).

Leaving group L is, for example, halogen such as chloro, fluoro, etc., (lower)alkanoyloxy such as acetoxy, etc., (lower) alkanesulfonyloxy such as methanesulfonyloxy, etc., arenesulfonyloxy such as p-toluenesulfonyloxy, etc., or alkoxycarbonyloxy.

The dotted line in the structure of formula (II) means that the compound of formula (II) can present as each of the compound of formula (II-a) or the compound of formula (II-b) or as a mixture of the compound of formula (II-a) and the compound of formula (II-b):

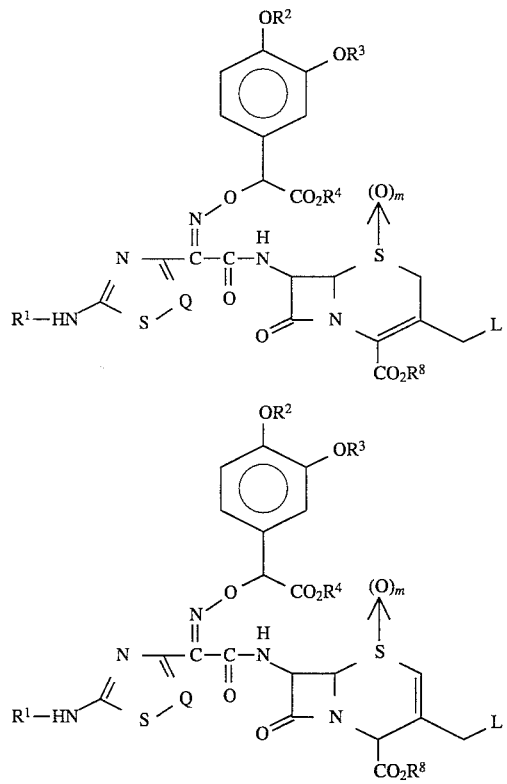

in which m, $R^1$, $R^2$, $R^3$, $R^4$, $R^8$, Q and L are defined as previously described.

The starting compound of formula (II) used in the present invention is a known compound and can be prepared according to the following reaction scheme. That is, the compound of formula (II) can be prepared by activating a compound having the following general formula (IV) or a salt thereof with an acylating agent and subsequently reacting the activated compound with a compound having the following general formula (V):

[Reaction Scheme]

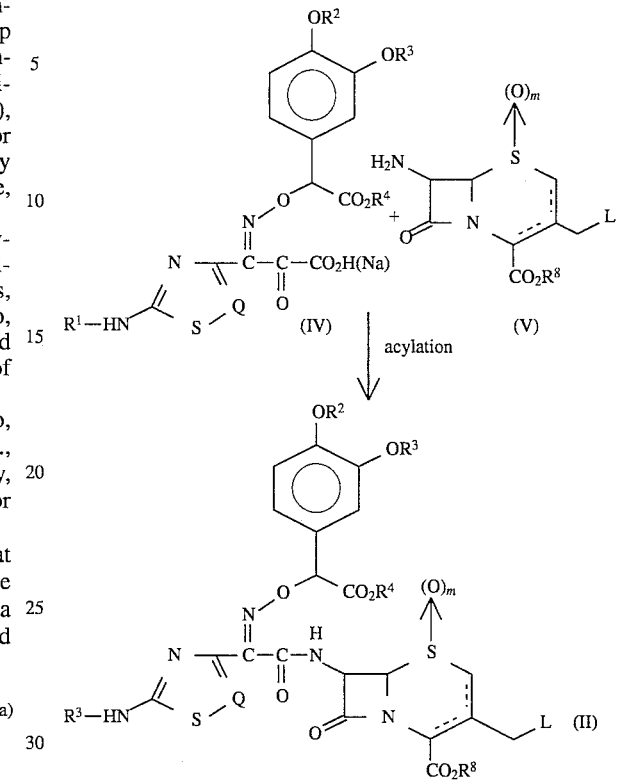

In the above reaction scheme, $R^1$, $R^2$, $R^3$, $R^4$, $R^8$, Q, m and L are defined as previously described.

The dotted line in the structure of formula (V) means that the compound of formula (V) can present as each of the compound of formula (V-a) or the compound of formula (V-b) or as a mixture of the compound of formula (V-a) and the compound of formula (V-b):

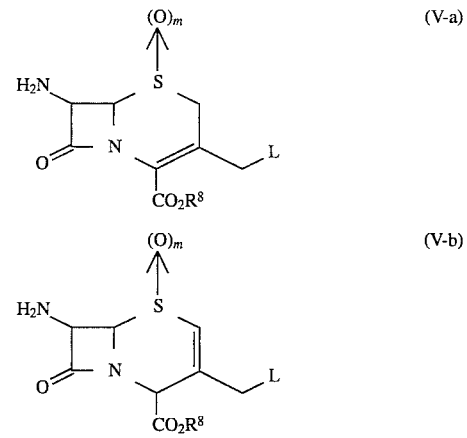

in which m, $R^8$ and L are defined as previously described.

In preparing the compound of formula (I), the amino-protecting group or the carboxyl-protecting group of the compound of formula (II) can be removed by a conventional method which has been well-known widely in cephalosporin field. Specifically, the protecting groups can be removed by hydrolysis or reduction. When the protecting groups contain an amino group, it is preferable to remove them by amino-halogenation or amino-etherification followed by hydrolysis. Acid hydrolysis is useful for removing tri(di)phenylmethyl or alkoxycarbonyl group and can be practiced by using an organic acid such as formic acid, trifluoroacetic acid, p-toluenesulfonic acid, etc, or an inorganic acid such as hydrochloric acid, etc.

The compound of formula (III) used in the present invention can be prepared according to the method described in Korean Patent Application Nos. 92-25647, 92-25307, 92-24735, 92-15176, and the like of the applicant of the present invention.

Meanwhile, in preparing the compound of formula (I) by substitution of the C-3 position of the compound of formula (II) with the compound of formula (III), the solvent which can be used includes a polar solvent such as N,N-dimethylformamide, dimethylsulfoxide, N,N-dimethylacetamide, methanol, etc. The reaction temperature is in the range of 10° C. to 80° C. and preferably of 20° C. to 40° C. The compound of formula (III) can be used in an amount of 0.5 to 2 equivalent weights, preferably 0.9 to 1.1 equivalent weights, with respect to the compound of formula (II).

The reaction product produced by the above reaction can be treated with various methods such as recrystallization, ionophoresis, silica gel column chromatography, ion-exchange resin chromatography and the like, to isolate and purify the desired compound of formula (I).

As described above, the compound of formula (I) shows a broad antibacterial spectrum and more potential antimicrobial activity against various pathogenic organisms including gram-positive and gram-negative strains. Such antimicrobial activity can also be applied to numerous gram-negative bacteria which produce β-lactamse. Accordingly, the compound of formula (I) can be effectively used for prophylaxis and treatment of bacterial infection in animals including human being.

The compound of formula (I) according to the present invention can be formulated according to the known method using known pharmaceutical carriers and excipients into a single dosage unit or to fill into a multiple-dose container. The formulation may be in the form of a solution, suspension or emulsion in oil or aqueous medium and can contain conventional dispersants, suspending agents or stabilizers. In addition, the formulation may be prepared in the form of a dry powder which can be dissolved in a pyrogen-free, sterilized water before use. The compound of formula (I) can also be formulated into a suppository using conventional suppository bases such as cocoa butter or other glycerides. If necessary, the compound of the present invention can be administered in a combination with other antibacterial agent such as penicillins or cephalosporins.

When the compound of the present invention is formulated into a single dosage unit, it is preferable that the single dosage unit contains about 50 to 1500 mg of the compound of formula (I) as an active ingredient. The dose of the compound of formula (I) to be administered should be dependent on various factors such as weight and age of individual patient and the condition and severity of disease. However, the daily dosage for adult patient is generally in the range of about 500 to 5000 mg depending on the administration frequency and route. When the compound of formula (I) is administered in intramuscular or intravenous injection, a total daily dosage of about 150 to 3000 mg is sufficient for adult patient. However, in the case of infections caused by some bacterial strains a more increased daily dosage may be preferable.

The compound of formula (I) and its non-toxic salts (preferably alkali metal salt, alkaline earth metal salt, inorganic acid addition salt, organic acid addition salt and salt with amino acid) according to the present invention are very useful for prophylaxis and treatment of diseases caused by bacterial infections in animals including human being, due to their potent antimicrobial activity against various pathogenic microorganisms including gram-positive and gram-negative bacterial strains.

Typical examples of the compound of formula (I) according to the present invention are listed on the following Table 1.

TABLE 1

| Compound No. | $R^1$ | $R^2$ | $R^3$ | Q |
|---|---|---|---|---|
| I-1(a) | (pyrimidinium with NH$_2$, CH$_3$, $^+$N-NH$_2$, NH$_2$ substituents) | —H | —H | CH |
| I-2(a) | (pyrimidinium with NH$_2$, $^+$N-NH$_2$, NH$_2$ substituents) | —H | —H | CH |
| I-3(a) | (pyrimidinium with NH$_2$, $^+$N-NH$_2$, NH$_2$ substituents) | —H | —H | CH |
| I-4(a) | (pyrimidinium with NH$_2$, $^+$N-NH$_2$ substituents) | —H | —H | CH |
| I-5(a) | (pyrimidinium with NH$_2$, $^+$N-NH$_2$ substituents) | —H | —H | CH |

TABLE 1-continued $$\text{(I)}$$

Structure (I): 3,4-bis(OR²,OR³)-phenyl-CH(OCO₂R⁴)-O-N=C(-CONH-[β-lactam-cephem core with SR¹])-C(NH₂)=N / S-Q ring

| Compound No. | R¹ | R² | R³ | Q |
|---|---|---|---|---|
| I-6(a) | [4-amino-pyridazinium with CO₂H substituent, N⁺-NH₂] | —H | —H | CH |
| I-7(a) | [4-amino-pyridazinium with CH₂SO₃H substituent, N⁺-NH₂] | —H | —H | CH |
| I-8(a) | [4-amino-pyridazinium fused cyclopentane, N⁺-NH₂] | —H | —H | CH |
| I-9(a) | [4-amino-pyridazinium fused with N=N ring] | —H | —H | CH |
| I-10(a) | [4-amino-pyridazinium fused with N-CH₃ / NH₂ ring] | —H | —H | CH |
| I-11(a) | [4-amino-pyridazinium fused with N—CH₃ pyrrole ring] | —H | —H | CH |

Hereinafter, the present invention will be more specifically explained on the basis of the following preparation examples and working examples. However, it should be understood that the technical scope of the present invention is not limited by these examples in any manner.

PREPARATION 1: Synthesis of 2-bromo-2-(3,4-O-isopropylidenedioxyphenyl)acetic acid diphenylmethyl ester A. Synthesis of 2-(3,4-dihydroxyphenyl)-2-hydroxy-1,1,1-trichloroethane To the solution of 440 g of 1,2-dihydroxybenzene dissolved in 1L of ethylene dichloride was added 1036 g of trichloroacetaldehyde monohydrate and then the reaction solution was cooled down to 0° C. 102 g of triethylamine was slowly added dropwise thereto. The reaction solution was warmed to normal temperature, stirred for about 20 minutes, heated to 50° C. and then stirred for further 3 hours while maintaining the same temperature. After the reaction is completed, the reaction mixture was distilled under reduced pressure to remove ethylene dichloride. The residue was dissolved in 4L of ethylacetate, washed successively with 2400 ml of 0.5N-aqueous hydrochloric acid solution and 2L of saturated saline solution, dried over anhydrous magnesium sulfate and then distilled under reduced pressure to remove the solvent to obtain 540 g of the title compound.

NMR ($\delta$, acetone-$d_6$): 5.2(d, 1H), 6.0(d, 1H), 6.8(d, 1H), 7.0(dd, 1H), 7.2(d, 1H), 7.9(s, 1H), 8.0(s, 1H)

B. Synthesis of α-trichloromethyl-3,4-isopropylidenedioxybenzyl alcohol 515 g of 2-(3,4-dihydroxyphenyl)-2-hydroxy-1,1,1-trichloroethane synthesized in Preparation i(A) was dissolved in 2.5L of benzene and then 305 ml of 2,2-dimethoxypropane and 2.84 g of phosphorus pentaoxide were added thereto. The reaction mixture was then heated under reflux. This reaction was carried out in a reaction vessel equipped with Soxhlet extractor wherein the extracting tube was filled with 600 g of calcium chloride to remove the reaction by-product, methanol. After 2 hours, 77 ml of 2,2-dimethoxypropane was added to the reaction vessel and the mixture was heated under reflux for further 3 hours. After the reaction is completed, the reaction solution was cooled to normal temperature, washed successively with 1N-aqueous sodium hydrogen carbonate solution (500 ml×4) and saturated saline solution (500 ml×4), dried over anhydrous magnesium sulfate and then distilled under reduced pressure to remove the solvent. The residue was purified by silica gel column chromatography to obtain 220 g of the oily title compound.

NMR (δ, CDCl$_3$): 1.66(6H, s), 3.61(d, 1H), 4.98(d, 1H), 6.53–6.90(m, 3H)

C. Synthesis of 2-(3,4-O-isopropylidenedioxyphenyl)-2-hydroxyacetic acid 119.4 g of lithium hydroxide monohydrate was dissolved in 500 ml of water and then cooled down to 0° C. To the resulting solution were added 201 g of α-trichloromethyl-3,4-isopropylidenedioxybenzyl alcohol prepared in Preparation i(B) and 413 ml of dioxane and the mixture was stirred at normal temperature for 3 days. After the reaction is completed, to the reaction solution was added 240 g of ice and then 3.00 ml of 6N-aqueous hydrochloric acid solution and 120 g of ice-water were added thereto. The mixture was stirred for 30 minutes to precipitate the solid product which was then filtered, washed with 1.8L of water and 700 ml of chloroform and dried under N$_2$ to obtain 60 g of the title compound.

NMR (δ, DMSO-d$_6$): 1.61(s, 6H), 4.85(s, 1H), 6.60–6.83(m, 3H), 8.2(bs, 2H)

D. Synthesis of 2-(3,4-O-isopropylidenedioxyphenyl)-2-hydroxyacetic acid diphenylmethyl ester 50 g of 2-(3,4-O-isopropylidenedioxyphenyl)-2-hydroxyacetic acid prepared in Preparation 1(C) was dissolved in 400 ml of acetone and then diazomethane dissolved in diethylether was added dropwise thereto until nitrogen is no more generated. After the addition is completed, the reaction mixture was stirred for further 20 minutes and then distilled under reduced pressure to remove the solvent. The residue was separated and purified by silica gel column chromatography to obtain 70 g of the title compound.

NMR (δ, CDCl$_3$): 1.69(s, 6H), 5.62(d, 1H), 6.20(d, 1H), 6.70(d, 1H), 6.87(s, 1H), 6.89(d, 1H), 6.97(s, 1H), 7.26(b, 10H)

E. Synthesis of 2-bromo-2-(3,4-isopropylidenedioxyphenyl)acetic acid diphenylmethyl ester 108 g of 2-(3,4-O-isopropylidenedioxyphenyl)-2-hydroxyacetic acid diphenylmethyl ester prepared in Preparation 1(D) was dissolved in 1.3L of dimethylformamide and then the reaction solution was cooled down to −60° C. 187.4 g of phosphorus tribromide was added thereto and then the temperature of the reaction solution was increased to −15° C. The reaction mixture was stirred for 20 minutes. After the reaction is completed, the reaction solution was distilled under reduced pressure to remove the solvent. The residue was dissolved in 1L of ethylacetate, washed with saturated saline solution (1L×4), dried over anhydrous magnesium sulfate and then distilled under reduced pressure to remove the solvent to obtain 115.96 g of the title compound.

NMR (δ, CDCl$_3$): 1.66(d, 6H), 5.41(s, 1H), 6.63(d, 1H), 6.84(s, 1H), 6.86(d, 1H), 6.97(s, 1H), 7.25(b, 10H)

PREPARATION 2: Synthesis of 2-)2-triphenylmethylaminothiazol-4-yl)-2-(α-diphenylmethyloxycarbonyl-3,4-O-isopropylidenedioxybenzyloxyimino)acetic acid

A. Synthesis of 2-(2-triphenylmethylaminothiazol-4-yl)-2-(α-diphenylmethyloxycarbonyl-3,4-O-isopropylidenedioxyimino)acetic acid allyl ester To the solution of 58.18 g of 2-(2-triphenylmethylaminothiazol-4-yl)-2-hydroxyiminoacetic acid allyl ester dissolved in 140 ml of dimethylformamide were added 61 g of potassium carbonate and 29.4 g of potassium iodide. The reaction solution was cooled down to 0° C. and then the solution of 80.16 g of 2-bromo-2-(3,4-O-isopropylidenedioxyphenyl)acetic acid diphenylmethyl ester prepared in Preparation 1(E) which is dissolved in 600 ml of dimethylformamide was added dropwise thereto over one hour. The reaction mixture was then stirred for further 20 minutes. After the reaction is completed, the reaction solution was distilled under reduced pressure to remove the solvent. The resulting solid was purified by silica gel column chromatography to obtain 89 g of the title compound.

NMR (δ, CDCl$_3$): 1.69(s, 6H), 4.81(d, 2H), 5.27(ABx, 2H), 5.79(s, 1 mH), 5.80–5.99(m, 6.53(s, 1H), 6.64(d, 1H), 6.78(d, 1H), 6.87(s, 1H), 7.13–7.36(m, 27H)

B. Synthesis of 2-(2-triphenylmethylaminothiazol-4-yl)-2-(α-diphenylmethyloxycarbonyl-3,4-O-isopropylidenedioxybenzyloxyimino)acetic acid 60 g of 2-(2-triphenylmethylaminothiazol-4-yl)-2-(α-diphenylmethloxycarbonyl-3,4-O-isopropylidenedioxybenzyloxyimino)acetic acid allyl ester prepared in Preparation 2(A) was dissolved in 500 ml of methylene dichloride. To the resulting solution were added 14.5 g of potassium 2-ethylhexanoate, 3.75 g of triphenylphosphine and 0.6 g of tetrakis (triphenylphosphine)palladium and the mixture was stirred at normal temperature for one hour. After the reaction is completed, the reaction solution was washed with saturated saline solution (500 ml×3), dried over anhydrous magnesium sulfate and then distilled under reduced pressure to remove the solvent. The residue was separated and purified by silica gel column chromatography to obtain 50 g of the title compound.

NMR (δ, CDCl$_3$): 1.70(s, 6H), 5.68(s, ms), 6.55(s, 1H), 6.66(d, 1H), 6.80(d, 1H), 6.89(s, 1H), 7.04–7.27(m, 27H)

PREPARATION 3: Synthesis of paramethoxybenzyl 3-chloromethyl-7-[(Z)-2-(α-diphenylmethyloxycarbonyl-3,4-O-isopropylidenedioxybenzyloxyimino)-2-(2-triphenylmethylaminothiazol-4-yl)acetamido]-3-cephem-4-carboxylate 36 g of paramethoxybenzyl 7-amino-3-chloromethyl-3-cephem-4-carboxylate was suspended in 950 ml of methylene dichloride and 28.1 g of pyridine was added thereto and then stirred until the intimate solution is formed. The reaction solution was cooled to −20° C. and 50.09 g of 2-(2-triphenylmethylaminothiazol-4-yl)-2-(α-diphenylmethyloxycarbonyl-3,4-O-isopropylidenedioxybenzyloxyimino)acetic acid prepared in Preparation 2(B) was added thereto. The reaction mixture was stirred for 5 minutes, and 13.62 g of phosphorus oxychloride was added thereto and then the mixture was stirred for further 30 minutes. After the reaction is completed, the reaction solution was washed with saturated saline solution (400 ml×3), dried over anhydrous magnesium sulfate and then distilled to remove the solvent. The resulting solid was purified by silica gel column chromatography to obtain 70 g of the title compound as a foamy solid.

NMR (δ, $CDCl_3$): 1.59(d, 6H), 3.33(ABq, 2H), 3.83(s, 3H), 4.51(ABq, 2H), 4.96(d, 1H), 6.27(s, 2H), 5.87(dd, 1H), 5.95(s, 1H), 6.6–7.45(m, 35H), 8.21(d, 1H)

Hereinafter, each compound of Examples 1 to 11 can be present as two diastereoisomers (R and S isomer). In addition, when the compound is subjected to high performance liquid chromatography using μ-Bondapak $C_{18}$ Steel column eluting with 25% methanol solution containing 0.5% acetic acid, the compounds having a short retention time and a long retention time were distinguished from each other by appending (a) and (b), respectively, to the number of each compound.

EXAMPLE 1: Synthesis of 7-[(Z)-2-(2-aminothiazol-4-yl)-2-(α-carboxy-3,4-dihydroxybenzyloxyimino)acetamido]-3-(5-methyl-1,4,6-triaminopyrimidinium-2-yl)thiomethyl-3-cephem-4-carboxylate I-1-a) and I-1-b)

2.0 g of methoxybenzyl 3-chloromethyl-7-[(Z)-2-(α-diphenylmethyloxycarbonyl-3,4 -O-isopropylidenedioxybenzyloxyimino)-2-(2-triphenylmethylaminothiazol-4-yl)acetamido]-3-cephem-4-carboxylate was dissolved in 10 ml of dimethylsulfoxide and then 420 mg of 5-methyl-1,4,6-triaminopyrimidin-2-thione was added thereto. Then the reaction mixture was stirred at normal temperature for 4 hours and 100 ml of distilled water was added thereto. The reaction solution was thoroughly stirred and then extracted with the mixed solvent of 30 ml of tetrahydrofuran and 50 ml of ethylacetate. The organic layer was separated and washed with saturated saline solution (100 ml×3). The organic layer thus obtained was dried over anhydrous magnesium sulfate, distilled under reduced pressure to remove the solvent and then dried to obtain the solid product which was then dissolved in 6 ml of anisole. The resulting solution was cooled down to 0° C. to 4° C. After adding dropwise 12 ml of trifluoroacetic acid, the mixture was stirred at room temperature for 2 hours and then cooled down to −20° C. to −30° C. To this reaction solution was added dropwise 50 ml of diethylether to precipitate the solid product which was then filtered, washed with acetone and dried to obtain 1.2 g of the pale yellow solid. The solid thus obtained was separated and purified by fractional liquid chromatography (μ-Bondapak $C_{18}$ Steel Column, 19 mm×30 mm) eluting with 10% aqueous methanol solution to obtain 40 mg and 30 mg of the title compounds I-1-a) and I-1-b), respectively, as a white solid.

(FAB, M+1): 719

NMR (δ, $D_2O$+$NaHCO_3$)

I-1(a): 1.85(s, 3H), 3.28(ABq, 2H), 4.16(ABq, 2H), 4.97(d, 1H), 5.40(s, 1H), 5.63(d, 1H), 6.78–6.97(m, 4H)

I-1-b): 1.83(s, 3H), 3.27(ABq, 2H), 4.19(ABq, 2H), 4.97(d, 1H), 5.40(s, 1H), 5.62(d, 1H), 6.78–7.02(m, 4H)

IR (KBr, $cm^{-1}$): 1770(β-lactam), 1680, 1610, 1530

EXAMPLE 2: Synthesis of 7-[(Z)-2-(2-aminothiazol-4-yl)-2-(α-carboxy-3,4-dihydroxybenzyloxyimino)acetamido]-3-(1,4,6-triaminopyrimidinium-2-yl)thiomethyl-3-cephem-4-carboxylate I-2(a) and I-2(b)

2.0 g of paramethoxybenzyl 3-chloromethyl-7-[(Z)-2-(α-diphenylmethyloxycarbonyl-3,4-O-isopropylidenedioxybenzyloxyimino)-2-(2-triphenylmethylaminothiazol-4-yl)acetamido]-3-cephem-4-carboxylate was dissolved in 10 ml of dimethylsulfoxide and then the reaction was carried out according to the same procedure as Example 1, except that 410 mg of 1,4,6-triaminopyrimidin-2-thione is used instead of 5-methyl-1,4,6-triamino-2-thione used in Example 1, to obtain 38 mg and 40 mg of the title compounds I-2(a) and I-2(b), respectively, as a white solid.

M.S. (FAB, M+1): 705

NMR (δ, $D_2O$+$NaHCO_3$)

I-2(a): 3.27(ABq, 2H), 4.17(ABq, 2H), 4.96(d, 1H), 5.40(s, 1H), 5.59(s, 1H), 5.63(d, 1H), 6.82–7.02(m, 4H)

I-2(b): 3.29(ABq, 2H), 4.18(ABq, 2H), 4.96(d, 1H), 5.40(s, 1H), 5.58(s, 1B), 5.68(d, 1H), 6.81–6.99(m, 4H)

IR (KBr, $cm^{-1}$): 1775 (β-lactam), 1670, 1620, 1570

EXAMPLE 3: Synthesis of 7-[(Z)-2-(2-aminothiazol-4-yl)-2-(α-carboxy-3,4-dihydroxybenzyloximio)acetamido]-3-(4,6-diamino-1-methylpyrimidinium-2-yl)thiomethyl-3-cephem-4-carboxylate I-3-(a) and I-3(b)

2.0 g of paramethoxybenzyl 3-chloromethyl-7-[(Z)-2-(α-diphenylmethyloxycarbonyl-3,4-O-isopropylidenedioxybenzyloxyimino)-2-(2-triphenylmethylaminothiazol-4-yl)acetamido]-3-cephem-4-carboxylate was dissolved in 10 ml of dimethylsulfoxide and then the reaction was carried out according to the same procedure as Example 1, except that 420 mg of 4,6-diamino-1-methylpyrimidin-2-thione is used instead of 5-methyl-1,4,6-triaminopyrimidin-2-thione used in Example 1, to obtain 42 mg and 38 mg of the title compounds I-3(a) and I-3(b), respectively, as a white solid.

M.S. (FAB, M+1): 704

NMR (δ, $D_2O$+$NaHCO_3$)

I-3(a): 3.35(ABq, 2H), 3.53(s, 3H), 4.24(ABq, 2H), 4.96(d, 1H), 5.38(s, 1H), 5.59(s, 1H), 5.64(d, 1H), 6.80–7.02(m, 4H)

I-3(b): 3.27(ABq, 2H), 3.45(s, 3H), 4.27(ABq, 2H), 4.96(d, 1H), 5.39(s, 1H), 5.51(s, 1H), 5.62(d, 1H), 6.79–7.04(m, 4H)

IR (KBr, $cm^-$): 1770(β-lactam), 1680, 1620, 1560

EXAMPLE 4: Synthesis of 7-[(Z)-2-(2-aminothiazol-4-yl)-2-(α-carboxy-3,4-dihydroxybenzyloxyimino)acetamide]-3-(1,4-diaminopyrimidinium-2-yl)thiomethyl-3-cephem-4-carboxylate I-4(a) and (-4(b)

2.0 g of paramethoxybenzyl 3-chloromethyl-7-[(Z)-2-(α-diphenylmethyloxycarbonyl-3,4-O-isopropylidenedioxybenzyloxyimino)-2-(2triphenylmethylaminothiazol-4-yl)acetamido]-3-cephem-4-carboxylate was dissolved in 10 ml of dimethylsulfoxide and then the reaction was carried out according to the same procedure as Example 1, except that 450 mg of 1,4-diaminopyrimidin-2-thione is used instead of 5-methyl-1,4,6-triaminopyrimidin-2-thione used in Example 1, to obtain 41 mg and 40 mg of the title compounds I-4(a) and I-4(b), respectively, as a white solid.

M.S. (FAB, M+1): 690

NMR (δ, $D_2O$+$NaHCO_3$)

I-4(a): 3.35(ABq, 2H), 4.27(ABq, 2H), 5.01(d, 1H), 5.42(s, 1H), 5.71(d, 1H), 6.52(d, 1H), 6.85–7.05(m, 4H), 7.98(d, 1H)

I-4(b): 3.27(ABq, 2H), 4.22(ABq, 2H), 4.95(d, 1H), 5.41(s, 1H), 5.62(d, 1H), 6.41(d, 1H), 6.82–7.04(m, 4H), 7.88(d, 1H)

IR (KBr, $cm^{-1}$): 1775(β-lactam), 1670, 1620, 1580

EXAMPLE 5: Synthesis of 7-[(Z)-2-(2-aminothiazol-4-yl)-2-(α-carboxy-3,4-dihydroxybenzyloxyimino)acetamido]-3-(4-amino-1-methylpyrimidinium-2-yl)thiomethyl-3-cephem-4-carboxylate I-5(a) and I-5(b)

2.0 g of paramethoxybenzyl 3-chloromethyl-7-[(Z)-2-(α-diphenylmethyloxycarbonyl-3,4-O-isopropylidenedioxy-benzyloxyimino)-2-(2-triphenylmethylaminothiazol-4-yl)acetamido]-3-cephem-4-carboxylate was dissolved in 10 ml of dimethylsulfoxide and then the reaction was carried out according to the same procedure as Example 1, except that 420 mg of 4-amino-1-methylpyrimidin-2-thione is used instead of 5-methyl-1,4,6-triaminopyrimidin-2-thione used in Example 1, to obtain 39 mg and 40 mg of the title compounds I5(a) and I-5(b), respectively, as a white solid.

M.S. (FAB, M+1): 689

NMR (δ, $D_2O$+$NaHCO_3$)

I-5(a): 3.32(ABq, 2H), 3.67(s, 3H), 4.32(ABq, 2H), 4.96(d, 1H), 5.39(s, 1H), 5.63(d, 1H), 6.47(d, 1H), 6.80–7.02(m, 4H), 7.81(d, 1H)

I-5(b): 3.31(ABq, 2H), 3.66(s, 3H), 4.31(ABq, 2H), 4.96(d, 1H), 5.36(s, 1H), 5.60(d, 1H), 6.45(d, 1H), 6.78–7.01(m, 4H), 7.80(d, 1H)

IR (KBr, $cm^{-1}$): 1775(β-lactam), 1680, 1630, 1590

EXAMPLE 6: Synthesis of 7-[(Z)-2-(2-aminothiazol-4-yl)-2-(α-carboxy-3,4-dihydroxybenzyloxyimino)acetamido]-3-(4-amino-1-methyl-5-carboxypyrimidinium-2-yl)thiomethyl-3-cephem-4-carboxylate I-6(a) I-6(b)

2.0 g of paramethoxybenzyl 3-chloromethyl-7-[(Z)-2-(α-diphenylmethyloxycarbonyl-3,4-O-isopropylidenedioxy-benzyloxyimino)-2-(2-triphenylmethylaminothiazol-4-yl)acetamido]-3-cephem-4-carboxylate was dissolved in 10 ml of dimethylsulfoxide and then the reaction was carried out according to the same procedure as Example 1, except that 430 mg of 4-amino-1-methyl-5-carboxypyrimidin-2-thione is used instead of 5-methyl-1,4,6-triaminopyrimidin-thione used in Example 1, to obtain 36 mg and 34 mg of the title compounds I-6(a) and I-6(b), respectively, as a white solid.

M.S. (FAB, M+1): 733

NMR (δ, $D_2O$+$NaHCO_3$)

I-6(a): 3.32(ABq, 2H), 3.79(s, 3H), 4.39(ABq, 2H), 4.97(d, 1H), 5.41(s, 1H), 5.64(d, 1H), 6.82–7.04(m, 4H), 8.37(s, 1H)

I-6(b): 3.35(ABq, 2H), 3.82(s, 2H), 4.38(ABq, 2H), 4.99(d, 1H), 5.42(s, 1H), 5.68(d, 1H), 6.83–7.02(m, 4H), 8.41(s, 1H)

(KBr, $cm^{-1}$): 1770(β-lactam), 1670, 1640, 1580

EXAMPLE 7: Synthesis of 7-[(Z)-2-(2-aminothiazol-4-yl)-2-(α-carboxy-3,4-dihydroxybenzyloxyimino)acetamido]-3-(1-methyl-4-amino-5-sulfomethylpyrimidinium-2-yl)thiomethyl-3-cephem-4-carboxylate I-7(a) and I-7(b)

2.0 g of paramethoxybenzyl 3-chloromethyl-7-[(Z)-2-(α-diphenylmethyloxycarbonyl- 3,4-O-isopropylidenedioxy-benzyloxyimino)-2-(2-triphenylmethylaminothiazol-4-yl)acetamido]-3-cephem-4-carboxylate was dissolved in 10 ml of dimethylsulfoxide and then the reaction was carried out according to the same procedure as Example 1, except that 430 mg of 1-methyl-4-amino-5-sulfomethylpyrimidin-2-thione is used instead of 5-methyl-1,4,6-triaminopyrimidin-2-thione used in Example 1, to obtain 35 mg and 36 mg of the title compounds I-7(a) and I-7(b), respectively, as a white solid.

(FAB, M+1): 783

NMR (δ, $D_2O$+$N_aHCO_3$)

I-7(a): 3.33(ABq, 2H), 3.64(s, 3H), 4.09(s, 2H), 4.34(ABq, 2H), 4.99(d, 1H), 5.42(s, 1H), 5.68(d, 1H), 6.83–7.03(m, 4H)

I-7(b): 3.32(ABq, 2H), 3.67(s, 3H), 4.10(s, 2H), 4.32(ABq, 2H), 4.97(d, 1H), 5.41(d, 1H), 5.66(d, 1H), 6.82–7.01(m, 4H)

(KBr, $cm^{-1}$): 1770(β-lactam), 1670, 1640, 1580

EXAMPLE 8: synthesis of 7-[(Z)-2-(2-aminothiazol-4-yl)-2-(α-carboxy-3,4-dihydroxybenzyloxyimino)acetamido]-3-(1,4-diamino-1,5,6,7-tetrahydrocyclopentapyrimidin-2-yl)thiomethyl-3-cephem-4-carboxylate I-8(a) and I-8(b)

2.0 g of paramethoxybenzyl 3-chloromethyl-7-[(Z)-2-(α-diphenylmethyloxycarbonyl-3,4-O-isopropylidenedioxy-benzyloxyimino)-2-(2-triphenylmethylaminothiazol-4-yl)acetamido]- 3-cephem-4-carboxylate was dissolved in 10 ml of dimethylsulfoxide and then the reaction was carried out according to the same procedure as Example 1, except that 420 mg of 1,4-diamino-1,5,6,7-tetrahydroxyclopentapyrimidin-2-thione is used instead of 5-methyl-1,4,6-triaminopyrimidin-2-thione used in Example 1, to obtain 43 mg and 42 mg of the title compounds I-8(a) and I-8(b), respectively, as a white solid.

M.S. (FAB, M+1): 730

NMR (δ, $D_2O$+$NaHCO_3$)

I-8(a): 2.22(m, 2H), 2.76(t, 2H), 3.08(t, 2H), 3.29(ABq, 2H), 4.32(ABq, 2H), 4.96(d, 1H), 5.40(s, 1H), 5.64(d, 1H), 6.82–6.98(m, 4H)

I-8(b): 2.23(m, 2H), 2.76(t, 2H), 3.06(t, 2H), 3.32(ABq, 2H), 4.35(ABq, 2H), 4.95(d, 1H), 5.41(s, 1H), 5.67(d, 1H), 6.81–6.98(m, 4H)

IR (KBr, $cm^{-1}$): 1775(β-lactam), 1670, 1620, 1560

EXAMPLE 9: Synthesis of 7-[(Z)-2-(2-aminothiazol-4-yl)-2-(α-carboxy-3,4-dihydroxybenzyloxyimino)acetamido]-3-(7-amino-1-1-methyl[1,2,4]triazolo[1,5-c]pyrimidinium-5-yl)thiomethyl-3-cephem-4-carboxylate I-9(a) and I-9(b)

2.0 g of paramethoxybenzyl 3-chloromethyl-7-[(Z)-2-(α-diphenylmethyloxycarbonyl-3,4-O-isopropylidenedioxybenzyloxyimino)-2-(2-triphenylmethylaminothiazol-4-yl)acetamido]-3-cephem-4-carboxylate was dissolved in 10 ml of dimethylsulfoxide and then the reaction was carried out according to the same procedure as Example 1, except that 440 mg of 7-amino-1-methyl[1,2,4]triazolo[1,5-c]pyrimidin-5-thione is used instead of 5-methyl-1,4,6-triaminopyrimidin-2-thione used in Example 1, to obtain 40 mg and 42 mg of the title compounds I-9(a) and I-9(b), respectively, as a white solid.

(FAB, M+1): 729

NMR ($\delta$, $D_2O$+NaHCO$_3$)

I-9(a): 3.32(ABq, 2H), 3.46(s, 3H), 4.35(ABq, 2H), 4.96(d, 1H), 5.40(s, 1H), 5.62(d, 1H), 6.26(s, 1H), 6.82–7.01(m, 4H), 8.64(s, 1H)

I-9(b): 3.34(ABq, 2H), 3.52(s, 3H), 4.37(ABq, 2H), 4.96(d, 1H), 5.41(s, 1H), 5.61(d, 1H), 6.27(s, 1H), 6.79–7.01(m, 4H), 8.62(s, 1H)

IR (KBr, cm$^{-1}$): 1770($\beta$-lactam), 1660, 1630, 1570

EXAMPLE 10: Synthesis of
7-[(Z)-2-(2-aminothiazol-4-yl)-2-($\alpha$-carboxy-3,4-dihydroxybenzyloxyimino)acetamido]-3-(2,7-diamino-1-methyl[1,2,4]triazolo[1,5-c]pyrimidinium-5-yl)thiomethyl-3-cephem-4-carboxylate I-10(a) and I-10(b)

2.0 g of paramethoxybenzyl 3-chloromethyl-7-[(Z)-2-($\alpha$-diphenylmethyloxycarbonyl-3,4-O-isopropylidenedioxybenzyloxyimino)-2-(2-triphenylmethylaminothiazol-4-yl)acetamido]-3-cephem-4-carboxylate was dissolved in 10 ml of dimethylsulfoxide and then the reaction was carried out according to the same procedure as Example 1, except that 440 mg of 2,7-diamino-1-methyl [1,2,4 ]triazolo[1,5-c]pyrimidin-5-thione is used instead of 5-methyl-1,4,6-triaminopyrimidin-2-thione used in Example 1, to obtain 41 mg and 40 mg of the title compounds I10(a) and I10(b), respectively, as a white solid.

M.S. (FAB, M+1): 744

NMR ($\delta$, $D_2O$+NaHCO$_3$)

I-10(a): 3.50(s, 3H), 3.37(ABq, 2H), 4.35(ABq, 2H), 4.96(d, 1H), 5.40(s, 1H), 5.64(d, 1H), 6.19(s, 1H), 6.78–6.96(m, 3H), 7.01(s, 1H)

I-10(b): 3.27(ABq, 2H), 3.44(s, 3H), 4.36(ABq, 2H), 4.95(d, 1H), 5.40(s, 1H), 5.58(d, 1H), 6.10(s, 1H), 6.79–6.98(m, 4H)

IR (KBr, cm$^{-1}$): 1775($\beta$-lactam), 1650, 1640, 1560

EXAMPLE 11: Synthesis of
7-[(Z)-2-(2-aminothiazol-4-yl)-2-($\alpha$-carboxy-3,4-dihydroxybenzyloxyimino)acetamido]-3-(7-amino-1-methyl-1H-imidazo[1,2-c]pyrimidinium-5-yl)-thiomethyl-3-cephem-4-carboxylate I-11(a) and I-11(b)

2.0 g of paramethoxybenzyl 3-chloromethyl-7-[(Z)-2-($\alpha$-diphenylmethyloxycarbonyl-3,4-O-isopropylidenedioxybenzyloxyimino)-2-(2-triphenylmethylaminothiazol-4-yl)acetamido ]-3-cephem-4-carboxylate was dissolved in 10 ml of dimethylsulfoxide and then the reaction was carried out according to the same procedure as Example 1, except that 430 mg of 7-amino-1-methyl-1H-imidazo[1,2c]pyrimidin-5-thione is used instead of 5-methyl-1,4,6-triaminopyrimidin-2-thione used in Example 1, to obtain 40 mg and 39 mg of the title compounds I-11(a) and I-11(b), respectively, as a white solid.

M.S. (FAB M+1): 728

NMR ($\delta$, $D_2O$+NaHCO$_3$)

I-11(a): 3.34(ABq, 2H), 3.68(s, 3H), 4.42(ABq, 2H), 4.96(d, 1H), 5.38(s, 1H), 5.63(d, 1H), 6.25(s, 1H), 6.83–7.01(m, 4H), 7.48(d, 1H), 7.54(d, 1H)

I-11(b): 3.27(ABq, 2H), 3.57(s, 3H), 4.37(ABq, 2H), 4.95(d, 1H), 5.35(s, 1H), 5.59(d, 1H), 6.10(s, 1H), 6.68–6.98(m, 4H), 7.26(d, 1H), 7.39(d, 1H)

(KBr, cm$^-$): 1770($\beta$-lactam), 1680, 1600, 1530

The pharmacological utility of the compound according to the present invention was estimated from the minimum inhibitory concentration against standard strain, strains resistant to some antibiotics and $\beta$-lactamse producing gram-negative strains and the pharmacokinetic properties in rats, as compared with Ceftazidime as the control medicine. The minimum inhibitory concentration was determined by diluting the test compounds according to 2-fold dilution, suspending them in Müller-Hinton agar medium, inoculating the test strains having $10^7$ CFU per 1 ml into the medium and then culturing the medium at 37° C. for 20 hours. The results are described in the following Table 2.

TABLE 2

| Minimum Inhibitory Concentration against standard strains (μg/ml) | | | | | | |
|---|---|---|---|---|---|---|
| Standard Strains/LK code | | I-1(a) | I-3(a) | I-4(a) | I-5(a) | I-6(a) |
| S. aureus | 6538pA | 0.25 | 0.5 | 1 | 0.5 | 2 |
| S. aureus | giorigio | 0.13 | 0.5 | 0.5 | 0.25 | 2 |
| S. faecalis | 29212A | 16 | 32 | 64 | 64 | 32 |
| E. coli | 10536 | 0.013 | 0.063 | 0.016 | 0.031 | 0.031 |
| E. coli | 3190Y | 0.063 | 0.031 | 0.063 | 0.063 | 0.13 |
| E. coli | TEM1 1193E | 0.063 | 0.063 | 0.063 | 0.063 | 0.063 |
| E. coli | TEM5 3739E | 0.25 | 0.5 | 0.5 | 0.5 | 0.25 |
| E. coli | TEM9 2639E | 1 | 4 | 1 | 2 | 4 |
| P. aeruginosa | 1912E | 0.5 | 0.5 | 0.25 | 0.5 | 0.25 |
| P. aeruginosa | 10145 | 0.25 | 0.5 | 0.25 | 0.5 | 0.25 |
| P. aeruginosa | 6065Y | 0.5 | 1 | 0.5 | 1 | 0.5 |
| A. calcoaceticus | 15473A | 0.5 | 0.5 | 0.25 | 0.5 | 0.5 |
| E. cloacae | 1194E | 1 | 8 | 1 | 4 | 4 |
| K. aerogenes | 1976E | 0.13 | 0.25 | 0.13 | 0.25 | 0.25 |
| S. marcescens | 1826E | 0.25 | 0.5 | 0.25 | 0.5 | 1 |
| S. typhimurium | 14028A | 0.063 | 0.063 | 0.031 | 0.031 | 0.031 |

TABLE 2-continued

| Minimum Inhibitory Concentration against standard strains (μg/ml) | | | | | | |
|---|---|---|---|---|---|---|
| Standard Strains/LK code | | I-7(a) | I-8(a) | I-10(a) | I-11(a) | *CAZ |
| S. aureus | 6538pA | 2 | 0.5 | 0.5 | 0.5 | 16 |
| S. aureus | giorigio | 2 | 0.063 | 0.25 | 0.5 | 4 |
| S. faecalis | 29212A | 32 | 16 | 8 | 8 | >128 |
| E. coli | 10536 | 0.031 | 0.031 | 0.016 | ≦0.008 | 0.13 |
| E. coli | 3190Y | 0.063 | 0.031 | 0.031 | 0.031 | 0.063 |
| E. coli | TEM1 1193E | 0.13 | 0.063 | 0.063 | 0.063 | 0.25 |
| E. coli | TEM5 3739E | 0.5 | 0.5 | 0.25 | 0.25 | 8 |
| E. coli | TEM9 2639E | 4 | 1 | 1 | 1 | >128 |
| P. aeruginosa | 1912E | 1 | 0.5 | 0.5 | 0.5 | 1 |
| P. aeruginosa | 10145 | 0.25 | 0.5 | 0.25 | 0.25 | 2 |
| P. aeruginosa | 6065Y | 1 | 1 | 0.5 | 0.5 | 32 |
| A. calcoaceticus | 15473A | 0.5 | 0.25 | 0.5 | 0.5 | 2 |
| E. cloacae | 1194E | 8 | 2 | 1 | 1 | 128 |
| K. aerogenes | 1976E | 0.5 | 0.13 | 0.13 | 0.13 | 0.25 |
| S. marcescens | 1826E | 1 | 0.5 | 0.25 | 0.25 | 0.25 |
| S. typhimurium | 14028A | 0.5 | 0.063 | 0.063 | 0.016 | 0.25 |

*CAZ: Ceftazidime

The pharmacokinetic properties of the compound of the present invention were determined using SD rats (♂) weighing 220 to 340 g. Specifically, the test samples were administered in intravenous route in an amount of 20 mg/kg to 2 to 5 test animals. Blood was taken from femoral vein every hours after the administration and then subjected to a biological assay using agar well method to measure the blood concentration. The results of pharmacokinetic properties calculated from the above blood concentration are described in the following Table 3.

TABLE 3

| Pharmacokinetic properties | | | | | |
|---|---|---|---|---|---|
| | Compound | | | | |
| Properties | I-1(a) | I-3(a) | I-4(a) | I-5(a) | I-6(a) |
| T½ (min) | 40 | 53 | 50 | 39 | 32 |
| AUC (μg, min/ml) | 3152 | 3324 | 3174 | 2614 | 2268 |

| | Compound | | | | |
|---|---|---|---|---|---|
| Properties | I-7(a) | I-8(a) | I-10(a) | I-11(a) | *CAZ |
| T½ (min) | 48 | 53 | 58 | 68 | 20 |
| AUC (μg, min/ml) | 3186 | 3868 | 3959 | 2873 | 1863 |

*CAZ: Ceftazidime

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A cephalosporin compound represented by the following formula (I):

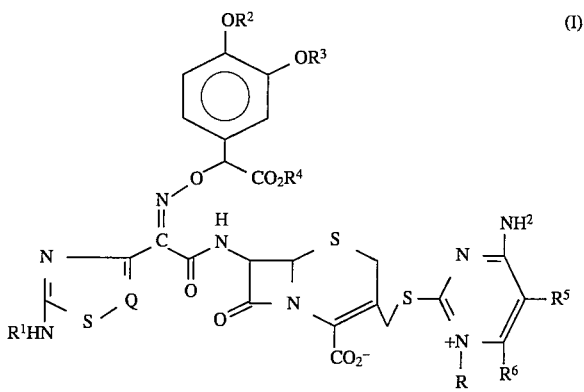

, its pharmaceutically acceptable non-toxic salt, physiologically hydrolyzable ester, hydrate and solvate and isomer thereof, in which $R^1$ represents hydrogen or an amino-protecting group, $R^2$ and $R^3$ can be identical or different and each represents hydrogen or a hydroxy-protecting group, or $R^2$ and $R^3$ together can form a diol-protecting cyclic group, $R^4$ represents hydrogen or a carboxyl-protecting group, $R^5$ represents hydrogen, $C_{1-4}$ alkyl, alkoxycarbonyl, carboxyl or sulfomethyl, $R^6$ represents hydrogen, amino or amino substituted with $C_{1-4}$ alkyl, and $R^7$ represents $C_{1-4}$ alkyl, amino or amino substituted with $C_{1-4}$ alkyl, or $R^5$ and $R^6$ together with the carbon atoms to which they are attached can form a cyclopentyl or cyclohexyl group, or $R^6$ and $R^7$ together with the carbon and nitrogen atoms to which they are attached can form a 3 to 7-membered heterocyclic ring which may optionally contain additional heteroatoms selected from nitrogen and/or oxygen and which may be substituted with a substituent selected from $C_{1-4}$ alkyl, amino and substituted amino, and Q represents CH or N.

2. The compound of formula (I) according to claim 1, wherein $R^1$ and $R^4$ independently of each other represent hydrogen, $R^2$ and $R^3$ are identical or different and represent hydrogen or acetyl, $R^5$ represents hydrogen, methyl, carboxyl or sulfomethyl, $R^6$ represents hydrogen or amino, $R^7$ represents methyl or amino, or $R^6$ and $R^7$ together with the carbon and nitrogen atoms to which they are attached may form imidazole or triazole which can have a substituent selected from methyl and amino.

3. A pharmaceutical composition comprising a therapeutically effective amount of the compound of formula (I), its pharmaceutically acceptable non-toxic salt, physiologically hydrolyzable ester, hydrate or solvate as defined in claim 1 or 2, together with a pharmaceutically acceptable carrier, excipient or additive.

\* \* \* \* \*